United States Patent [19]

Schüller

[11] Patent Number: 5,607,457

[45] Date of Patent: Mar. 4, 1997

[54] PACEMAKER WITH EVOKED RESPONSE DETECTION BY USING DIFFERENTIAL SENSING BETWEEN TWO UNIPOLAR ELECTRODES

[76] Inventor: Hans Schüller, S-224 67 Lund, Jullovsvägen 25, Sweden

[21] Appl. No.: 536,453

[22] Filed: Sep. 29, 1995

[51] Int. Cl.⁶ .................................................. A61N 1/368
[52] U.S. Cl. ........................................................ 607/9
[58] Field of Search ............................. 607/4, 7, 9, 11, 607/17, 18; 128/696, 697

[56] References Cited

U.S. PATENT DOCUMENTS

| | | | |
|---|---|---|---|
| 4,708,144 | 11/1987 | Hamilton et al. | 128/696 |
| 4,712,554 | 12/1987 | Garson, Jr. | 607/9 |
| 4,779,617 | 10/1988 | Whigham | 607/9 |
| 4,898,182 | 2/1990 | Hawkins et al. | 128/696 |
| 4,945,917 | 8/1990 | Akselrod et al. | 128/696 |
| 5,265,602 | 11/1993 | Anderson et al. | 607/9 |
| 5,365,932 | 11/1994 | Greenhut | 128/696 |
| 5,417,716 | 5/1995 | Franberg et al. | 607/9 |
| 5,522,855 | 6/1996 | Hoegnelid | 607/9 |

FOREIGN PATENT DOCUMENTS 0479215  8/1992  European Pat. Off. ............... 607/9

*Primary Examiner*—William E. Kamm
*Assistant Examiner*—George R. Evanisko
*Attorney, Agent, or Firm*—Hill, Steadman & Simpson

[57] ABSTRACT

A heart stimulator, operable for single-chamber and/or dual-chamber pacing, includes first and second electrical leads connected to a pulse generator and each terminating in an electrode, the electrodes being disposed respectively in the atrium and the ventricle. A differential detector is connected to the first and second leads and detects cardiac activity between the atrial electrode and the ventricular electrode. A correlation detector is connected between the pacemaker housing and one of the atrial or ventricular electrodes, and generates a correlation signal identifying whether the cardiac activity detected by the cardiac activity detector arose in the atrium or in the ventricle. The outputs of the differential detector and the correlation detector are supplied to a logic circuit which determines therefrom whether a stimulation pulse emitted by the pulse generator resulted in an evoked response in the heart.

26 Claims, 5 Drawing Sheets

PACEMAKER WITH EVOKED RESPONSE DETECTION BY USING DIFFERENTIAL SENSING BETWEEN TWO UNIPOLAR ELECTRODES

BACKGROUND OF THE INVENTION

1. Field of the Invention

The present invention is directed to a heart stimulator having two unipolar electrodes respectively arranged in the atrium and ventricle of a heart, for detecting atrial and ventricular activity and for pacing the heart at those locations.

2. Description of the Prior Art and Related Application

Pacemakers which supply pacing pulses both to the atrium and to the ventricle of a heart, as well as sensing cardiac activity in each of those chambers, and which supply pacing pulses only in the absence of a natural heartbeat are widely used for treating patients with bradycardia. Such pacemakers are known as DDD pacemakers, and require two electrodes, respectively disposed in the atrium and ventricle, each with its own lead.

By supplying artificial stimulation pulses from the pacemaker only in the absence of a natural heartbeat, battery current is conserved. Moreover, the ability to detect an evoked response, following an artificially generated stimulation pulse, permits the energy content of the pulse to be adjusted so as to be just at the capture threshold, i.e., having the minimum energy content which is necessary to evoke a pacing response in the heart. This avoids the generation of pulses having an energy which is higher than necessary to produce the desired response, thereby further contributing battery conservation.

Such evoked response detection requires relatively complicated electronic circuitry compared to conventional pacemakers, because such circuitry must, within a few tens of milliseconds after the delivery of an artificial pacing pulse, having an amplitude on the order of one volt sense/detect, a cardiac signal on the order of some millivolts.

Two basic approaches have been undertaken in the art to sense cardiac activity within the heart and to deliver stimulation pulses, generated by circuitry contained within an implanted pacemaker enclosure, to the heart in vivo. One approach has been to use two separate unipolar electrode leads, one having an electrode disposed in the atrium and the other having an electrode disposed in the ventricle. Pacing and detection than takes place between the respective electrode and the metallic pacemaker enclosure. The other basic approach has been to use two bipolar electrode leads respectively disposed in the atrium and the ventricle. A bipolar lead carries two electrodes or electrically active surfaces, such as an electrode ring and an electrode tip. Both the electrode ring and the electrode tip are disposed in the heart.

In the case of unipolar systems, it is possible that interference may be sensed along with the cardiac signal, such interference arising on, or related to, the metallic pacemaker enclosure. Although the bipolar approach minimizes the presence of such interference in the final signal, bipolar electrodes are more complicated than unipolar electrodes, because of the necessity of having at least two electrical conductors therein.

A heart stimulator is disclosed in co-pending U.S. patent application Ser. No. 467,267, filed Jun. 6, 1995 ("Heart Stimulator," Hoegnelid et al), that application being a continuation of Ser. No. 147,744, filed Nov. 4, 1993 and now abandoned. The teachings of this co-pending application are incorporated herein by reference. This copending application discloses a heart stimulator having a pulse generator and an electrode system which contains at least one bipolar electrode with one pole arranged in the atrium and one pole in the ventricle, or at least two unipolar electrodes respectively arranged in the atrium and ventricle, for detecting atrial and ventricular activity, and having an atrial measurement unit arranged to measure a signal between the two poles of the bipolar electrode, or between the two unipolar electrodes, and a ventricular measurement unit arranged to measure a signal between the ventricular pole (or electrode) and the stimulator housing. This co-pending application is owned by the same assignee (Pacesetter AB) as the subject matter of the present application.

SUMMARY OF THE INVENTION

It is an object of the present invention to provide a pacemaker wherein stimulation and sensing takes place using two unipolar electrodes, one electrode placed in the right atrium, and the other placed in the right ventricle, wherein sensing takes place without significant interference.

The above object is achieved in accordance with the principles of the present invention in a cardiac pacemaker having two unipolar electrodes for sensing cardiac activity (as well as for use in delivering stimulation pulses) the electrodes being respectively disposed in the right atrium and the right ventricle of a heart, with the electrical signals corresponding to cardiac activity being differentially sensed between these electrodes and wherein the sensed signal is additionally subjected to correlation detection in order to identify which electrode is the source for the incoming signal.

The signal which is used for correlation detection is a unipolar signal, and thus may have interference associated therewith, however, since this signal is only used as an identifier for the source of the signal which is differentially detected, the possible presence of interference does not, in most circumstances impair this function.

The pacemaker disclosed herein has the advantage of permitting technically simple electrodes, i.e., unipolar electrode leads, to be used, but permits an evoked cardiac signal to be detected without interference arising due to the use of unipolar electrodes for sensing.

The pacemaker disclosed herein is a dual chamber pacemaker, i.e., it can be operated so as to deliver artificial stimulation pulses both in the atrium and the ventricle of a heart. Stimulation occurs between one of the unipolar electrodes and the pacemaker metallic enclosure. Cardiac signals sensing occurs between the two unipolar electrodes, and between one of the electrodes and the pacemaker enclosure. The circuitry contained within the pacemaker enclosure includes a switching network for delivering a stimulation pulse with a rapid discharge of the residual polarization arising on the electrode as a result of the delivery of the stimulation pulse. For detecting the cardiac signal, amplifiers with adapted signal filters and a signal detector are provided. The signal detector includes a switching network for minimizing the influence from the stimulation pulse and from the residual polarization on the detection. The signal detectors senses signals between the two electrodes, and another signal detector, the correlation detector, senses signals between either the stimulating electrode or the other (temporarily) non-stimulating electrode, and the pacemaker enclosure. The signal detection which takes place in the first signal detector indicates if a stimulation pulse has actually stimulated the cardiac tissue and resulted in an evoked response. The stimulation energy can be regulated in order to make the next pulse more efficient, if necessary. The correlation detection provides a signal which identifies which of the unipolar electrodes was the source of the evoked signal.

Pacing may be in the form of sequential stimulation both in the atrium and in the ventricle, with appropriate switching being made within the pacemaker enclosure in order to permit the signal sensing to be undertaken. Alternatively, the pacemaker can be operated to pace only in the atrium or only in the ventricle.

DESCRIPTION OF THE PREFERRED EMBODIMENTS

Figure 1:
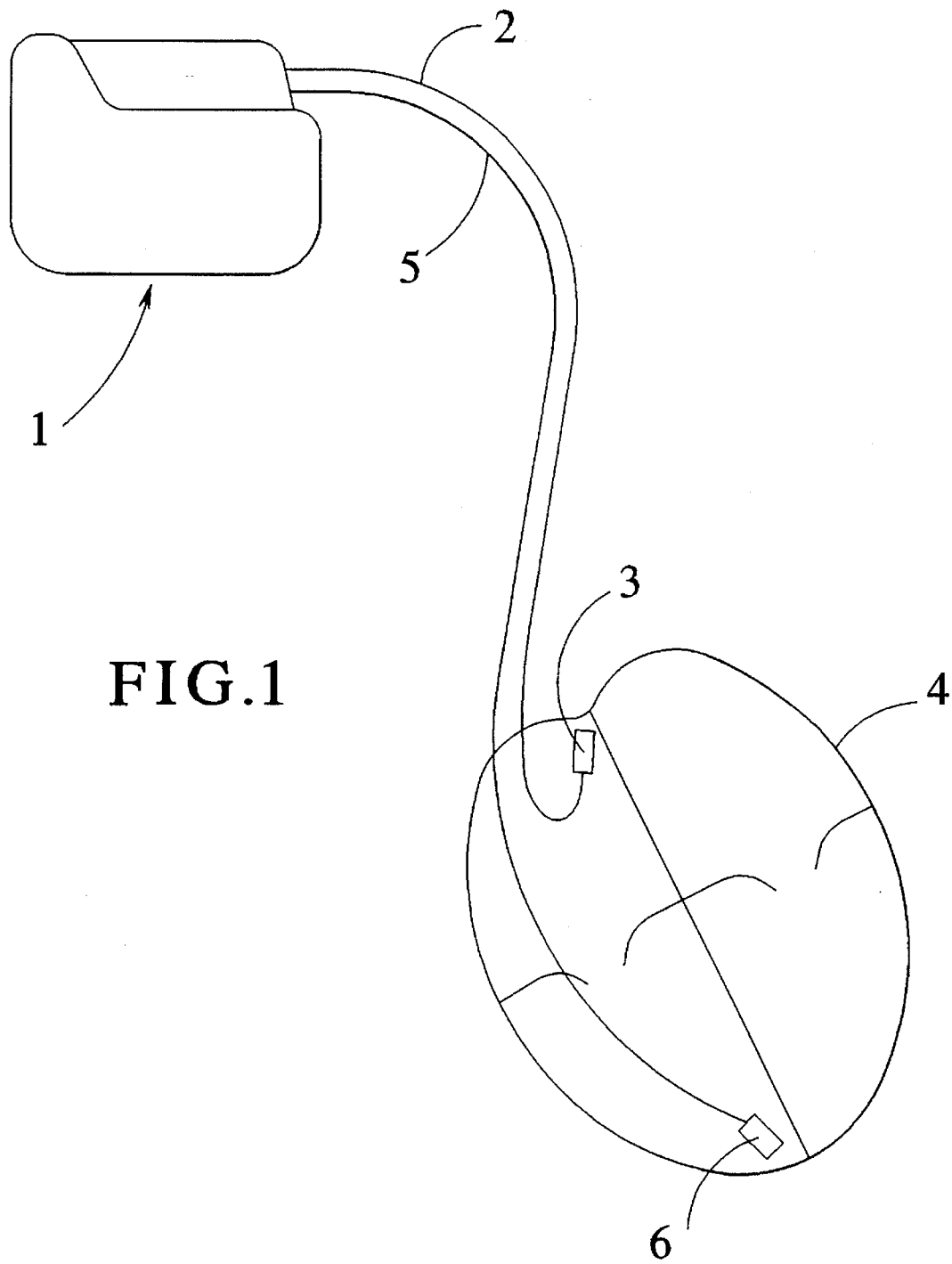
FIG. 1 illustrates the connection of a pacemaker constructed in accordance with the principles of the present invention to a heart.

FIG. 1 illustrates an implantable pacemaker 1 for stimulating and sensing cardiac activity in vivo in a (schematically illustrated) heart 4. The pacemaker 1 is in electrical connection with the heart 4 by means of a unipolar atrial lead 2 and a unipolar ventricular lead 5. The atrial lead 2 terminates in an electrode 3 disposed at a suitable location in the right atrium of the heart 4, and the ventricular lead 5 terminates in an electrode 6 disposed at a suitable location in the right ventricle of the heart 4. The respective positions of the electrodes 3 and 6 within the heart 4 shown in FIG. 1 are for exemplary purposes only; the electrodes 3 and 6 can be placed at any suitable locations respectively in the right atrium and the right ventricle in accordance with the physiology and pacing therapy associated with a particular patient. Moreover, only one lead and electrode may be used (active) i.e., only the atrial electrodes 3 or only the ventricular electrode 6, in the case of single-chamber pacing, although both leads and electrodes will still be present.

Figure 2:
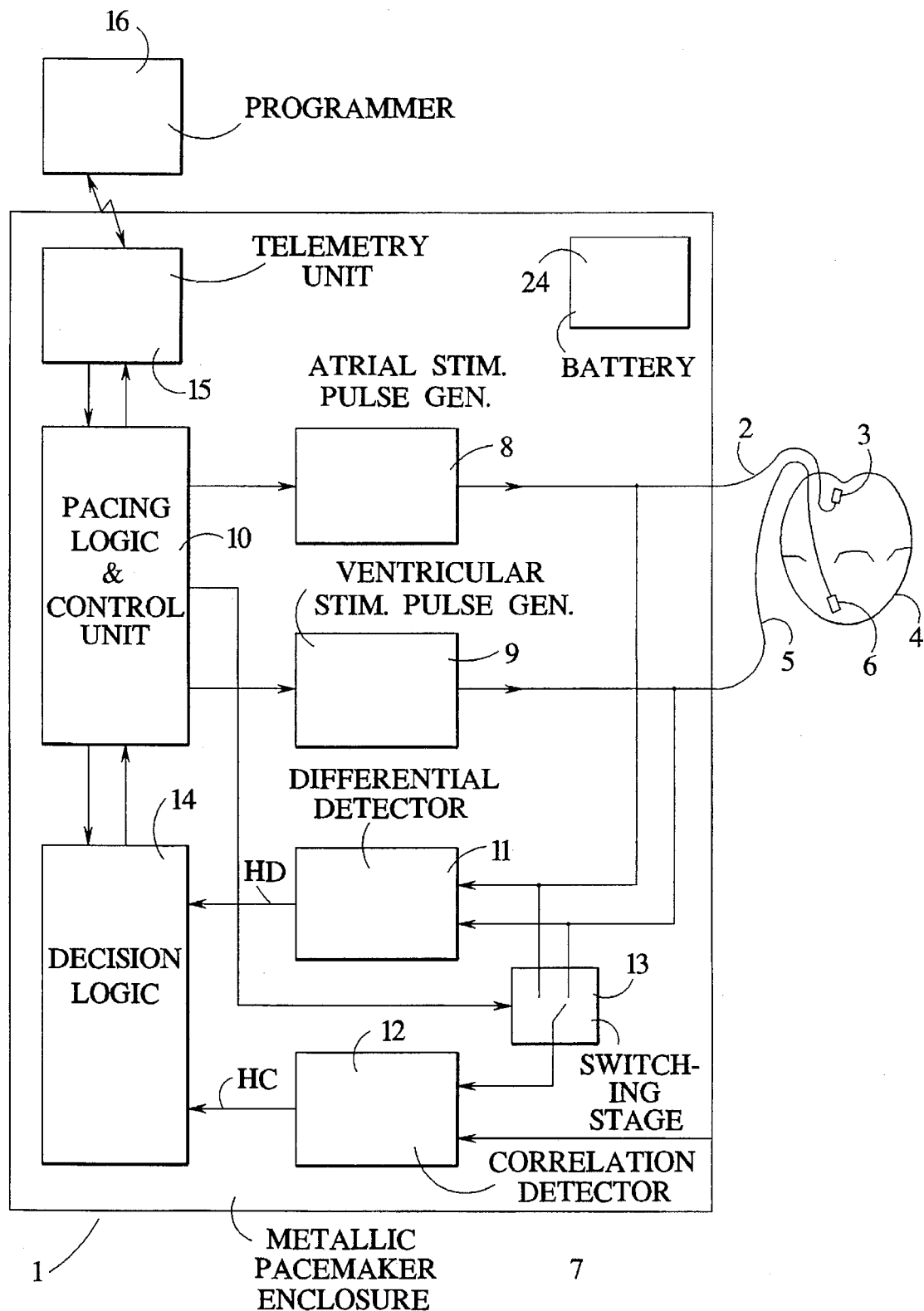
FIG. 2 is a block circuit diagram of the basic components of a pacemaker constructed in accordance with the principles of the present invention, connected to a heart.

The basic components of the implantable pacemaker 1 are shown in FIG. 2, in accordance with the principles of the present invention. The pacemaker 1 has a metallic pacemaker enclosure 7 to which the leads 2 and 5 are mechanically and electrically connected in a known manner (not shown in greater detail). Electrical pulses for artificially stimulating the atrium of the heart 4 are generated by an atrial stimulation pulse generator 8, connected to the atrial lead 2, and are delivered to the right atrium via the lead 2 and the electrode 3. In a similar manner, ventricular stimulation pulses are generated by a ventricular stimulation pulse generator 9, and are supplied to the right ventricle of the heart 4 via the ventricular lead 5 and the electrode 6. The duration, energy content, rate and other standard features of the atrial and ventricular stimulation pulses are set by means of a pacing logic and control unit 10, connected to the atrial stimulation pulse generator 8 and to the ventricular stimulation pulse generator 9. The pacing logic and control unit 10 contains all of the necessary, known electronics, which may include a microprocessor and a memory, for operating a programmable implanted pacemaker.

Detection of atrial and ventricular cardiac events also takes place via the unipolar leads 2 and 5. For this purpose, the atrial lead 2 is connected to a differential detector 11 and, via a switching stage 13, to a correlation detector 12. The ventricular lead 5 is also connected to the differential detector 11 and is also connected, via the switching stage 13, to the correlation detector 12 via the same input as the atrial lead 2. The other input to the correlation detector 12 is connected to the metallic pacemaker enclosures 7. Detecting therefore always takes place in the differential detector 11 between the atrial electrode 3 and the ventricular electrode 6, whereas detection in the correlation detector 12 takes place, depending on the state of the switching stage 13, between the atrial electrode 3 and the pacemaker enclosure 7, or between the ventricular electrode 6 and the pacemaker enclosure 7. The state of the switching stage 13 is controlled by a signal supplied from the pacing logic and control unit 10 generated as a part of the operating program. The switching stage 13 may, for example, be a suitable network of switching transistors.

The output of the differential detector 11 is a heart differential signal HD and the output of the correlation detector 12 is a heart signal correlation HC. The signals HD and HC are both supplied to decision logic 14 which, as described in more detail below, not only identifies whether an evoked response has occurred following an artificial stimulation of either the ventricle or the atrium, but also identifies the source of the evoked response, i.e., whether it was detected by the atrial electrode 3 or by the ventricular electrode 6. Activity detected by the atrial electrode 3 is assumed to represent atrial activity, and activity detected by the ventricular electrode 6 is assumed to be ventricular activity. The decision logic 14 is in two-way communication with the pacing logic and control unit 10 so that the decision logic 14 is informed by the pacing logic and control unit 10 when an artificial atrial pulse or an artificial ventricular pulse has been caused to be emitted by one of the pulse generators 8 or 9, and so that the pacing logic and control unit 10 can be informed by the decision logic 14 if an evoked response has occurred.

All components shown in FIG. 2 are supplied with power from a battery 24 contained in the pacemaker enclosure 7. Electrical connections from the battery 24 to each of the components are not separately shown, these being well known to those of ordinary skill in the art. The pacing logic and control unit 10 contains standard circuitry for setting the energy content of the atrial and ventricular pulses respectively generated by the pulse generators 8 and 9 so as to be just enough to evoke an appropriate response upon delivery of those pulses to the heart 4, thereby conserving the power of the battery 24. The pacing logic and control unit 10 also includes suitable demand circuitry so that pulses are caused to be emitted by the pulse generators 8 and 9 only in the absence of natural or spontaneous atrial and/or ventricular activity. The pacing logic and control unit 10 can, per programmed instructions, operate the pulse generators 8 and/or 9 for single-chamber or dual-chamber pacing.

The pacing logic and control unit 10 is also for two-way communication with a telemetry unit 15, the telemetry unit 15, in turn, being in communication with an extracorporeal programmer 16, such as by RF communication. The programmer 16 is used not only to program the operation of the pacemaker 1, but also to enter new or updated operating parameters into the pacing logic and control unit 10 for use in the operating program. The programmer 16 is also used to periodically download accumulated, stored historical information regarding the operation of the pacemaker 1, and the state of the heart 4, over an extended period of time.

Figure 3:
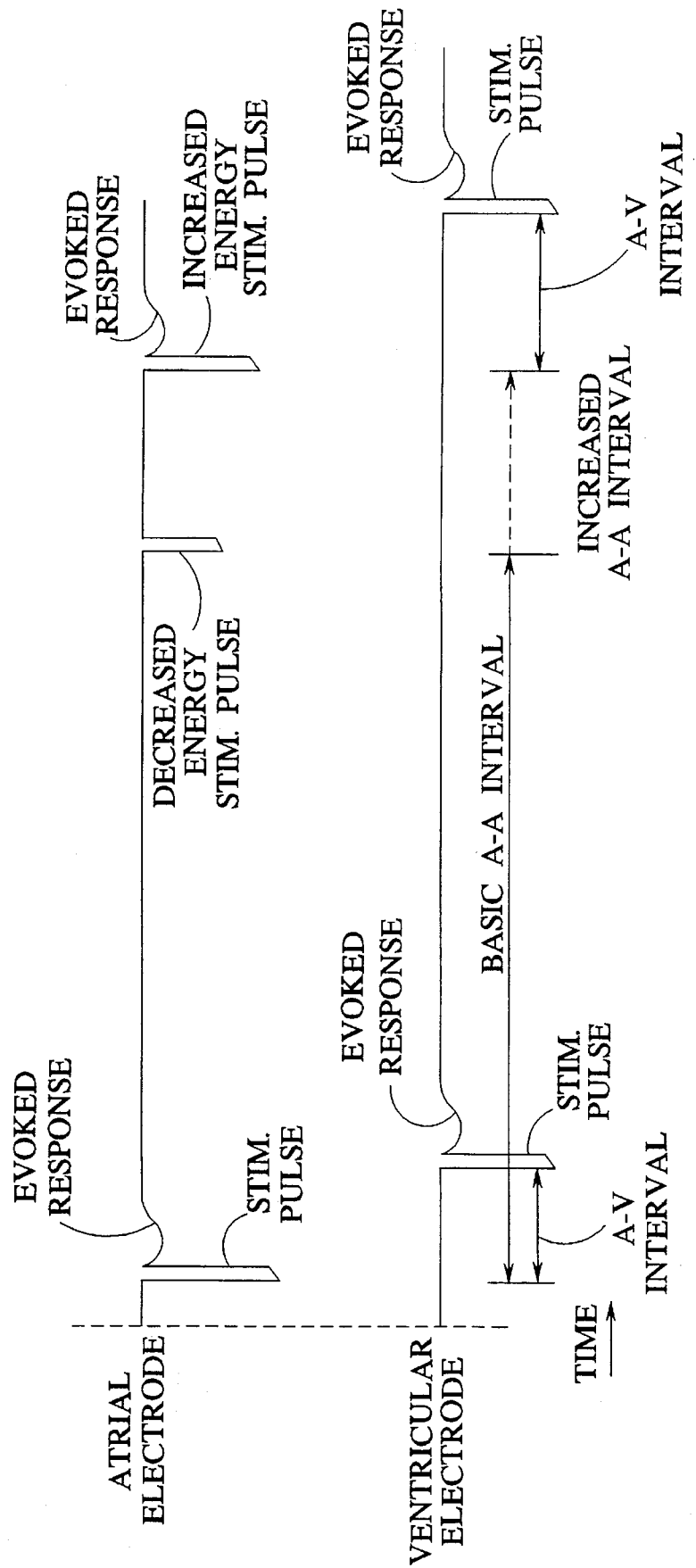
FIG. 3 illustrates voltages arising on the atrial electrode and on the ventricle electrode during operation of the pacemaker shown in FIG. 2.

Exemplary signals appearing on the atrial electrode 2 and the ventricular electrode 6 are shown in FIG. 3 to provide a brief explanation of the manner by which the amplitude of the stimulation pulses can be adjusted so as to be set at an energy content which is just high enough to cause an evoked response in the heart 4. In the example of FIG. 3, it is assumed that only the pulses supplied to the atrium via the atrial lead 2 and the atrial electrode 3 are being varied, however, the same principle applies to the pulses supplied via the ventricular lead 5 and the ventricular electrode 6. As shown in FIG. 3, a first stimulation pulse at the left of FIG. 3 is emitted by the atrial stimulation pulse generator 8, having a first amplitude, and this pulse results in an evoked response being detected, also via the atrial lead 2, in the manner described below. Following a programmed AV interval, a ventricular stimulation pulse is caused by the pacing logic and control unit 10 to be emitted by the ventricular stimulation pulse generator 9. This pulse is delivered via the ventricular lead 5 and the ventricular electrode 6 to the heart 4, and this pulse also results in an evoked response being detected. After a programmed, basic A—A interval, the next atrial stimulation pulse is caused by the pacing logic and control unit 10 to be emitted by the atrial stimulation pulse generator 8. In the generation of this second atrial stimulation pulse, however, the atrial stimulation pulse generator 8 has been instructed by the pacing logic and control unit 10 to emit a pulse having a slightly lower amplitude, and thus a lower energy content, in comparison to the previous atrial stimulation pulse. (It will be understood that the energy content could alternatively be varied by emitting a second atrial pulse having the same amplitude, but of shorter duration.)

In the example of FIG. 3, the second atrial stimulation pulse does not have a sufficient energy content to evoke a response in the heart 4, and thus no evoked response signal follows the second atrial stimulation pulse. This results in the basic A—A interval being slightly increased, due to the need to generate an "extra" stimulation pulse. A third atrial stimulation pulse is thereby caused to be generated by the atrial stimulation pulse generator 8, with a larger energy content. In the example of FIG. 3, this third atrial stimulation pulse again causes an evoked response, which is detected. After the programmed AV interval, a second ventricular pulse is thereby caused to be emitted.

Once an energy content of a stimulation pulse is determined, which is sufficient to consistently evoke the desired cardiac response, all following pulses can be consistently emitted with this same energy content, or a continuous testing of the capture threshold can be undertaken as described above. Combinations of these two approaches can also be employed, for example, testing of the capture level can be undertaken periodically, such as once a day, once a week, etc., and between each test, the energy content delivered per pulse remains the same.

Figure 4:
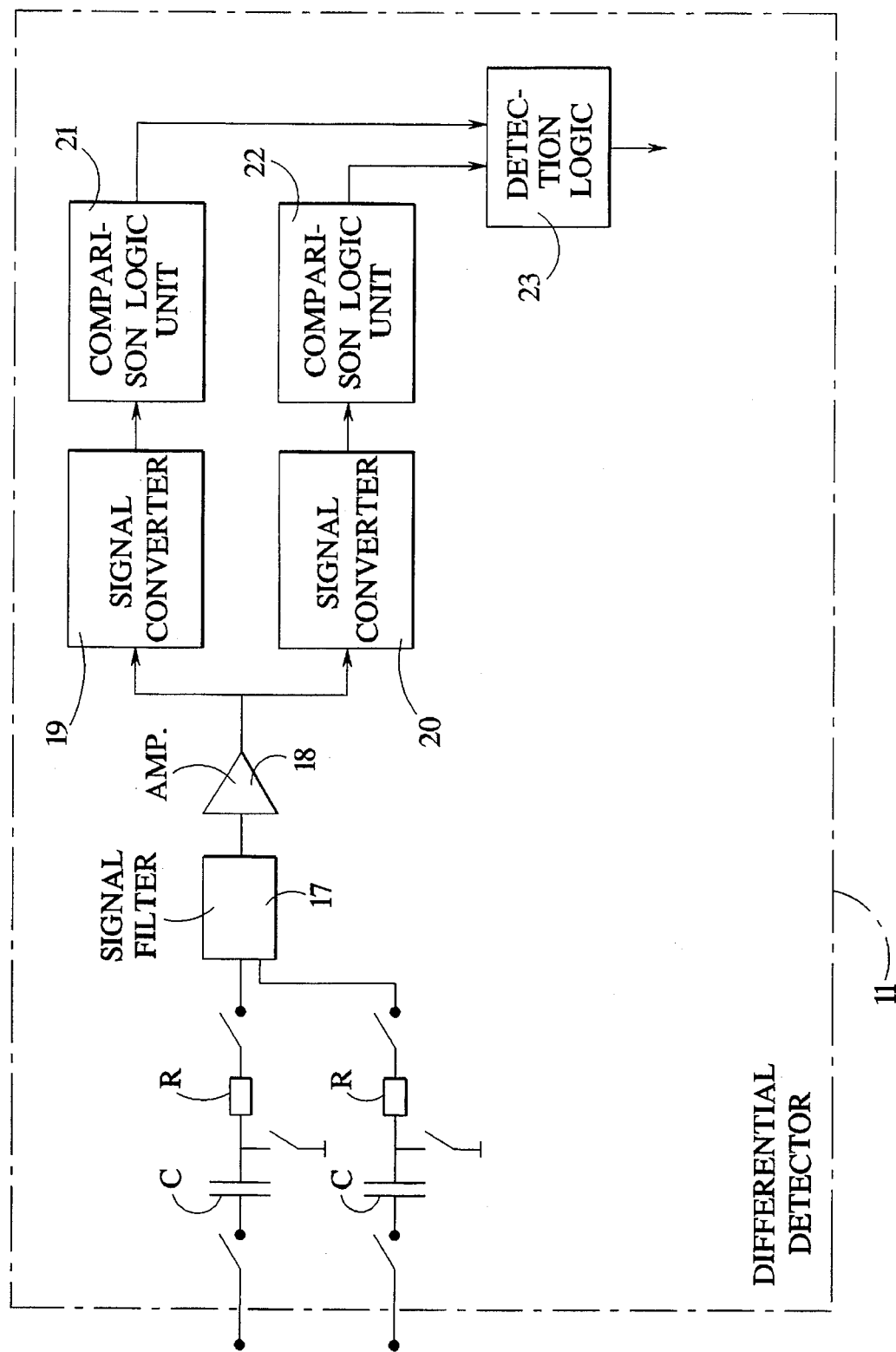
FIG. 4 is a block circuit diagram of each of the differential detector and the correlation detector shown in FIG. 2.

The basic components of each of the differential detector 11 and the correlation detector 12 are shown in FIG. 4. These two detectors are identically constructed, however, for exemplary purposes, the differential detector 11 is shown in FIG. 4. As noted above, in the case of the differential detector 11, the two input signals will be signals which are respectively detected by the atrial electrode 3 and the ventricular electrode 6. In the case of the correlation detector 12, one input will always be connected to the pacemaker enclosure 7, whereas the other input will either be supplied from the atrial electrode 3 or the ventricular electrode 6, depending upon the state of the switching stage 13. The incoming signals in each of the detectors 11 and 12 are first supplied to a decoupling stage formed by switches, capacitors and resistors in a known manner. The switches are preferably switching transistors, which are operated by the pacing logic and control unit 10 so as to be open only during, and for a short time after, the emission of an artificial stimulation pulse, in order to avoid charging and saturation of the following input amplifier. The resistors and capacitors which are present in this network also afford some filtering characteristics.

The incoming signals are then supplied to a signal filter 17, wherein remaining undesired signals can be filtered out of the incoming signal, and other suitable signal editing can also be undertaken in a known manner similar to the operation of a differential amplifier. The filtering can be undertaken with analog techniques, or by sampled digital filters.

The output of the signal filter 17 is supplied to an amplifier 18 (although it is equally possible for amplification to take place preceding the signal filter 17). Amplification is normally needed to boost the low level incoming signals, which are on the order of a few millivolts, to a signal level on the order of one volt.

The filtered and amplified signal is then supplied to first and second signal converters 19 and 20. The signal converter 19 may, for example, be a differentiator which takes the first derivative of the incoming signal, in which case the signal converter 20 will be a differentiating unit which takes the second derivative of the incoming signal. Alternatively, the signal converter 19 can be an integrator which integrates the incoming signal once, and the signal converter 20 can be an integrator which doubly integrates the incoming signal.

It is possible to practice the invention using only one signal converter, i.e. a single differentiator or a single integrator, however, the use of dual signal converters 19 and 20 allows more information to be obtained regarding the incoming signal, and thus a more reliable detection algorithm can be employed. If only a single signal conversion is to be undertaken, moreover, this could be accomplished within the signal filter 17, and a separate signal converter would then not be necessary.

In the exemplary embodiment of FIG. 4 employing two signal converters 19 and 20, the respective outputs of those converters are supplied to first and second comparator logic units. Depending on a predetermined or programmable comparison of the respective outputs of the signal converters 19 and 20 to comparison criteria, the comparator logic units 21 and 22 respectively emit high or low logic signals depending on whether the comparison criteria have been met. In the simplest case, the comparison criterion in each comparison logic unit 21 and 22 is a threshold level, and if the signal from the respective signal converters 19 and 20 exceeds the threshold level, this is an indication tending toward the presence of an evoked response. More complicated comparison criterion may be employed, however, such as requiring the presence of a sequence of signal features which exceed a predetermined threshold or other known criteria.

The outputs of the comparator logic units 21 and 22 are supplied to a detection logic unit 23. If only one signal converter and only one comparator logic unit are employed, then the output of the comparator logic unit becomes the output of the differential detector 11 (or correlation detector 12), and the detection logic unit 23 is not necessary. In the exemplary embodiment of FIG. 4, however, wherein two signal converters 19 and 20 and two comparison logic units 21 and 22 are employed, the detection logic unit 23 generates a high logic output if the signals at its inputs satisfy predetermined, or programmed, detection criteria, such as both inputs being high, or at least one input being high. If both inputs are low, no evoked response is assumed to have occurred. The output of the detection logic unit 23, in this case the signal HD, is then supplied to the decision logic 14.

Because the detection takes place in the subject matter disclosed herein using differential signals respectively obtained via unipolar electrodes in the atrium and the ventricle, the detection is substantially free of external signal interference, because such interference, if it exists, is present in substantially the same degree in each incoming signal, and thus is substantially canceled or eliminated during the differential detection. Because the detection is differential, however, it is not possible to determine with certainty, simply by means of the differential detection, whether the incoming signal originated in the atrium or in tile ventricle. The origin of the incoming signal may be inferred due to the timing of the detection, however, in order to improve the accuracy in the identification of the origin of the detected signal, the correlation detector 12 is provided. The only function of the correlation detector 12 is to determine from which chamber the incoming signal originated, or at least two assign an origin to the incoming signal with the highest probability. The decision logic 14, based on the signals HD and HC supplied thereto, determines, also using the timing signals supplied thereto by the pacing logic and control unit 10, what heart activity has been detected. The detected activity may be a spontaneous heartbeat either in the atrium or in the ventricle, or an evoked heartbeat from one of the chambers, produced by an artificially generated atrial or ventricular stimulation pulse. Any information used by the pacing logic and control unit 10 to set the timing of the artificially generated pulses (time measurements of escape intervals, refractory times, the time at which stimulation pulses are caused to be emitted, etc.) can be supplied from the pacing logic and control unit 10 to the decision logic 14 to assist in identifying the type of activity which has been detected.

FIGS. 5–11 show various possibilities for the signals HD and HC produced by different types of cardiac activity. In FIGS. 5–8, the downwardly extending portion symbolically illustrates the form of a marker pulse emitted when the pacing logic and control unit 10 causes either the atrial stimulation pulse generator 8 to emit an atrial pulse, or the ventricular stimulation pulse generator 9 to emit a ventricular pulse. Moreover, in FIGS. 5–11, the respective outputs of the differential detector 11 (i.e. the signal HD) and the correlation detector 12 (i.e., the signal HC) are :shown as positive logic pulses. A pulse produced by the differential detector 11 indicates the detection of any type of evoked response, and a pulse emitted by the correlation detector 12 is caused either by the particular chamber to which it is connected, or from interference. In the representative signals shown in FIGS. 5–11, it is assumed that the correlation detector 12 is connected between the ventricle (i.e., the ventricular electrode 6) and the pacemaker enclosure 7.

Figure 5:
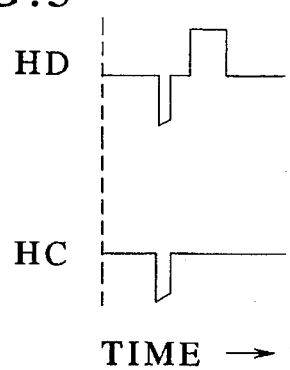
FIG. 5 shows the respective outputs of the differential detector and the correlation detector in the circuit of FIG. 2 in the presence of an evoked response following an artificial atrial stimulation.
Figure 6:
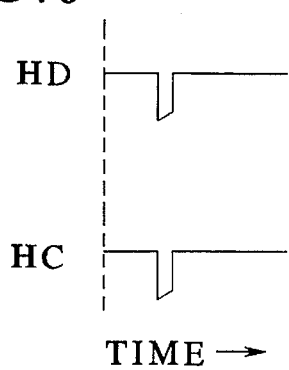
FIG. 6 shows the respective outputs of the differential detector and the correlation detector in the circuit of FIG. 2 in the case of no evoked response following an artificial atrial stimulation.

In the exemplary signals shown in FIGS. 5 and 6, the presence of the marker pulse indicates that an artificial atrial stimulation pulse was generated, and FIG. 5 shows the signal HD when an evoked response occurs, and FIG. 6 shows the signal HD in the absence of an evoked response. As can be seen in FIGS. 5 and 6, an evoked response does not cause any pulse to be included in the signal HC.

Figure 7:
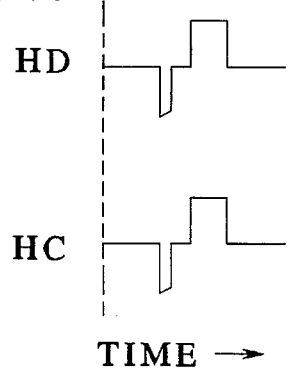
FIG. 7 shows the respective outputs of the differential detector and the correlation detector in the circuit of FIG. 2 in the presence of an evoked response following an artificial ventricular stimulation.
Figure 8:
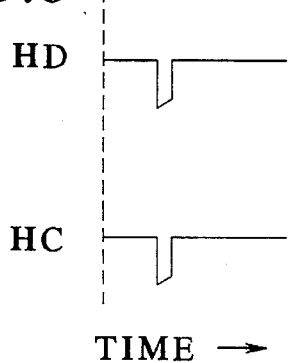
FIG. 8 shows the respective outputs of the differential detector and the correlation detector in the circuit of FIG. 2 in the case of no evoked response following an artificial ventricular stimulation.

A similar situation with respect to the ventricle is shown in FIGS. 7 and 8, wherein the marker pulse indicates the delivery of an artificial ventricular stimulation pulse, and FIG. 7 shows the presence of an evoked response in the signal HD, and FIG. 8 shows the absence of an evoked response in signal HD. Since the correlation detector 12 is connected to the ventricle, the evoked ventricular response causes a pulse to be present in the HC signal, as shown in FIG. 7.

Figure 9:
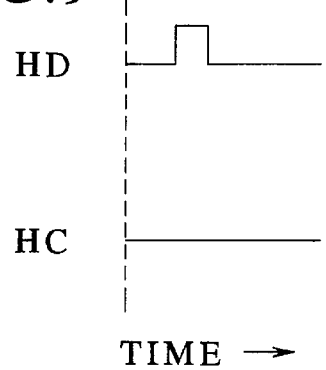
FIG. 9 shows the respective outputs of the differential detector and the correlation detector in the circuit of FIG. 2 in the presence of a spontaneous atrial signal.

FIG. 9 shows the signals in the case of a spontaneous atrial contraction, and thus no marker pulse is present since no artificial pulse was generated. Again, however, the atrial response results in a pulse being present in the signal HD of FIG. 9, but no such pulse is present in the signal HC.

Figure 10:
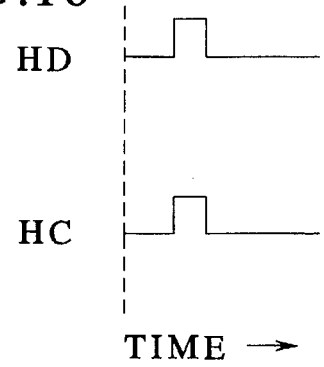
FIG. 10 shows the respective outputs of the differential detector and the correlation detector in the circuit of FIG. 2 following a spontaneous ventricular heart signal.

The signals in the case of a spontaneous ventricular contraction are shown in FIG. 10, resulting in a pulse being present in each of the signals HD and HC.

Figure 11:
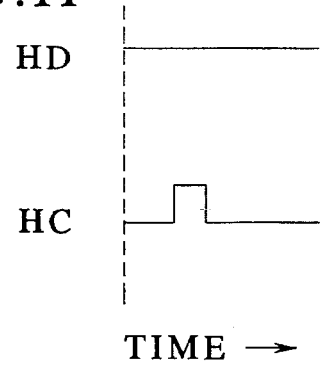
FIG. 11 illustrates the respective outputs of the differential detector and the correlation detector in the circuit of FIG. 2 in the presence of external interference.

Lastly, FIG. 11 shows in example of the signals HD and HC in the presence of external interference, which may arise from external electrical sources or skeletal muscles. Such external interference will result in a pulse or a train of pulses being generated by the correlation detector 12, which is present in the signal HC, however, the interference has no effect on the signal HD.

Although modifications and changes may be suggested by those skilled in the art, it is the intention of the inventors to embody within the patent warranted hereon all changes and modifications as reasonably and properly come within the scope of their contribution to the art.

I claim as my invention:

1. A heart stimulator comprising:

a housing implantable in a subject;

pulse generator means contained in said housing for emitting stimulation pulses;

a first unipolar electrical lead electrically connected to said pulse generator means for receiving said stimulation pulses therefrom, and terminating in an atrial placeable electrode placeable in the atrium of a heart of said subject;

a second unipolar electrical lead electrically connected to said pulse generator means for receiving said stimulation pulses therefrom, and terminating in a ventricular electrode placeable in the ventricle of said heart;

control means for controlling said pulse generator means for causing said stimulation pulses to be delivered to at least one of the atrium and the ventricle;

means in said housing connected to said first and second electrical leads for differentially detecting cardiac activity between said atrial electrode and said ventricular electrode and generating an electrical cardiac activity signal corresponding to said cardiac activity;

means in said housing, connected between said housing and one of said atrial or ventricular electrodes, for generating a correlation signal identifying whether said cardiac activity detected by said means for differentially detecting cardiac activity arose in the atrium or in the ventricle; and logic means, supplied with said cardiac activity signal and said correlation signal, for determining from said cardiac activity signal and said correlation signal whether a stimulation pulse emitted by said pulse generator means resulted in an evoked response in said heart.

2. A heart stimulator as claimed in claim 1 further comprising switching means for selectively connecting said means for generating a correlation signal between said housing and said atrial electrode or between said housing and said ventricular electrode.

3. A heart stimulator as claimed in claim 1 wherein said means for differentially detecting cardiac activity comprises:

editing means having a first input connected to said first electrical lead and a second input connected to said second electrical lead for producing an edited signal from a signal across said first and second inputs;

signal converter means for converting said edited signal into a converted signal having a characteristic associated therewith which changes dependent on whether an evoked response has resulted following emission of a stimulation pulse by said pulse generator means;

comparator means for comparing said characteristic to a predetermined threshold and emitting an output signal dependent on a value of said characteristic relative to said threshold, said output signal comprising said cardiac activity signal.

4. A heart stimulator as claimed in claim 3 wherein said editing means includes means for filtering said signal across said first and second inputs.

5. A heart stimulator as claimed in claim 3 wherein said editing means includes means for amplifying said signal across said first and second inputs.

6. A heart stimulator as claimed in claim 3 wherein said signal converter means comprises means for differentiating said edited signal.

7. A heart stimulator as claimed in claim 3 wherein said signal converter means comprises means for integrating said edited signal.

8. A heart stimulator as claimed in claim 3 wherein said editing means comprises means for forming a difference between said first and second inputs.

9. A heart stimulator as claimed in claim 1 wherein said means for detecting cardiac activity comprises:

editing means having a first input connected to said first electrical lead and a second input connected to said second electrical lead for producing an edited signal from a signal across said first and second inputs;

first signal converter means for converting said edited signal into a first converted signal, having a first parameter which changes dependent on whether an evoked response resulted following emission of a stimulation pulse by said pulse generator means;

first comparator means for comparing said first characteristic to a first threshold and for emitting a first output signal dependent on a value of said first characteristic relative to said first threshold;

second signal converter means for converting said edited signal into a second converted signal, having a second characteristic, different from said first characteristic, which changes dependent on whether an evoked response resulted following emission of a stimulation pulse by said pulse generator means;

second comparator means for comparing said second characteristic to a second threshold and for emitting a second output signal dependent on a value of said second characteristic relative to said second threshold; and detection logic means, supplied with said first and second output signals, for generating said cardiac activity signal dependent on said first and second output signals.

10. A heart stimulator as claimed in claim 9 wherein said editing means includes means for filtering said signal across said first and second inputs.

11. A heart stimulator as claimed in claim 9 wherein said editing means includes means for amplifying said signal across said first and second inputs.

12. A heart stimulator as claimed in claim 9 wherein said first signal converter means comprises means for generating a first derivative of said edited signal, and wherein said second signal converter means comprises means for generating a second derivative of said edited signal.

13. A heart stimulator as claimed in claim 9 wherein said first signal converter means comprises means for singly integrating said edited signal, and wherein said second signal converter means comprises means for doubly integrating said edited signal.

14. A heart stimulator as claimed in claim 9 wherein said editing means comprises means for forming a difference between said first and second inputs.

15. A heart stimulator as claimed in claim 1 wherein said means for generating a correlation signal comprises:

editing means having a first input connected to one of said first or second electrical leads and a second input connected to said housing for producing an edited signal from a signal across said first and second inputs;

signal converter means for converting said edited signal into a converted signal having a characteristic associated therewith which changes dependent on whether an evoked response has resulted following emission of a stimulation pulse by said pulse generator means;

comparator means for comparing said characteristic to a predetermined threshold and emitting an output signal dependent on a value of said characteristic relative to said threshold, said output signal comprising said correlation.

16. A heart stimulator as claimed in claim 15 wherein said editing means includes means for filtering said signal across said first and second inputs.

17. A heart stimulator as claimed in claim 15 wherein said editing means includes means for amplifying said signal across said first and second inputs.

18. A heart stimulator as claimed in claim 15 wherein said signal converter means comprises means for differentiating said edited signal.

19. A heart stimulator as claimed in claim 15 wherein said signal converter means comprises means for integrating said edited signal.

20. A heart stimulator as claimed in claim 15 wherein said editing means comprises means for forming a difference between said first and second inputs.

21. A heart stimulator as claimed in claim 1 wherein said means for generating a correlation signal comprises:

editing means having a first input connected to one of said first or second electrical leads and a second input connected to said housing for producing an edited signal from said first and second inputs;

first signal converter means for converting said edited signal into a first converted signal, having a first parameter which changes dependent on whether an evoked response resulted following emission of a stimulation pulse by said pulse generator means;

first comparator means for comparing said first characteristic to a first threshold and for emitting a first output signal dependent on a value of said first characteristic relative to said first threshold;

second signal converter means for converting said edited signal into a second converted signal, having a second characteristic, different from said first characteristic, which changes dependent on whether an evoked response resulted following emission of a stimulation pulse by said pulse generator means;

second comparator means for comparing said second characteristic to a second threshold and for emitting a second output signal dependent on a value of said second characteristic relative to said second threshold; and detection logic means, supplied with said first and second output signals, for generating said correlation signal dependent on said first and second output signals.

22. A heart stimulator as claimed in claim 21 wherein said editing means includes means for filtering said signal across said first and second inputs.

23. A heart stimulator as claimed in claim 21 wherein said editing means includes means for amplifying said signal across said first and second inputs.

24. A heart stimulator as claimed in claim 21 wherein said first signal converter means comprises means for generating a first derivative of said edited signal, and wherein said second signal converter means comprises means for generating a second derivative of said edited signal.

25. A heart stimulator as claimed in claim 21 wherein said first signal converter means comprises means for singly integrating said edited signal, and wherein said second signal converter means comprises means for doubly integrating said edited signal.

26. A heart stimulator as claimed in claim 21 wherein said editing means comprises means for forming a difference between said first and second inputs.

* * * * *